(12) United States Patent
Sato et al.

(10) Patent No.: US 6,326,006 B1
(45) Date of Patent: Dec. 4, 2001

(54) BATHING PREPARATION

(75) Inventors: Hirotaka Sato; Hidenori Yorozu; Masatomo Ando; Yoshinori Nishizawa, all of Tochigi (JP)

(73) Assignee: Kao Corporation, Tokyo (JP)

( * ) Notice: Subject to any disclaimer, the term of this patent is extended or adjusted under 35 U.S.C. 154(b) by 1366 days.

(21) Appl. No.: 08/655,490

(22) Filed: May 30, 1996

Related U.S. Application Data

(63) Continuation of application No. 07/794,851, filed on Nov. 21, 1991, now abandoned, which is a continuation of application No. 07/401,695, filed on Sep. 1, 1989, now abandoned.

(30) Foreign Application Priority Data

| Sep. 2, 1988 | (JP) | 63-219878 |
| Apr. 21, 1989 | (JP) | 1-103069 |

(51) Int. Cl.$^7$ ................................. A61K 35/78
(52) U.S. Cl. ....................... 424/195.1; 252/173
(58) Field of Search .................. 252/173, DIG. 5; 424/195.1; 514/783; 549/307

(56) References Cited

U.S. PATENT DOCUMENTS

| 55,474 | * | 6/1866 | Eisenhut | 424/195.1 |
| 58,106 | * | 9/1866 | Kieffer | 424/195.1 |
| 83,273 | * | 10/1868 | Fullerton | 424/195.1 |
| 94,466 | * | 9/1869 | Becker | 424/195.1 |
| 120,705 | * | 11/1871 | Brecht | 424/195.1 |
| 132,424 | * | 10/1872 | Wollenweber | 424/195.1 |
| 143,427 | * | 10/1873 | Stützel | 424/195.1 |
| 201,194 | * | 3/1878 | Normand | 424/195.1 |
| 392,776 | * | 11/1888 | Bizzozero | 424/195.1 |
| 2,489,972 | * | 11/1949 | Mowry | 549/307 |

FOREIGN PATENT DOCUMENTS

| 86172181 | * | 10/1984 | (JP) | 424/195.1 |
| 1103833 | * | 5/1986 | (JP) | 424/195.1 |
| 63246319A | * | 10/1988 | (JP) | 424/195.1 |

OTHER PUBLICATIONS

Patent Abstracts of Japan, vol. 13, No. 49 (C–565) [3397] Abstract of JPA 63–246 319.
Patent Abstracts of Japan, vol. 11, No. 63 (C–406) [2510] Abstract of JPA 61–225,117.
Patent Abstracts of Japan, vol. 11, No. 141 (C–421) [2588] Abstract of JPA 61–280,417.
Patent Abstracts of Japan, vol. 10, No. 78 (C–335) [2135] Abstract of JPA 60–215 618.
Patent Abstracts of Japan, vol.13, No. 515 (C–655( [3863] Abstract of JPA 1–207 233.
Chemical Abstracts, vol. 88, No. 19, May 8, 1978, p.18 Abstract No. 130721p.
Chemical Abstracts, vol. 83, No. 10, Sep. 8, 1975, p. 362, Abstract No. 84751v.
Chemical Abstracts, vol. 109, No. 23, Dec. 5, 1988, p. 398, Abstract No. 208257r.
Chemical Abstracts, vol. 107, No. 18, Nov. 2, 1987, Abstract No. 161766x.
Chemical Abstracts, vol. 92, No. 21, May 26, 1980, p. 329, Abstract No. 177412m.
Encyclopedia of Chemical Technology vol. 7 John Wiley and Sons pp. 166–168.*
Modern Cosmeticology vol. 1 By Wilkinson, chemical publishing Co., 1962 pp. 444–451.*
Bull. Inst. Chem, Acad Sin 31, 9–15, 1984.*
Gold et al. Alkylidene Phthalides and Dinyrophthalides From Celery, J Org Chem 28 985 (1963).*
Lin Lung–Ching, Synthesis, Properties and Molecular Structure of Alkylidene Phthalides Bull. Inst. Chem ACA Sin 31 9–15 Mar. 1984 pp. 9–15.*
Wilkinson J.B., Modern Cosmeticology vol. 1 Chemical Publishing Co NY 1962 pp. 444–451.*
Lin, L.C. Synthesis, Properties and Molecular structure of Alklidenephthalides, Bull Inst Chem 31 pp. 9–15 Mar. 1984.*

* cited by examiner

*Primary Examiner*—Ralph Gitomer
(74) *Attorney, Agent, or Firm*—Sughrue, Mion, Zinn, Macpeak & Seas, PLLC

(57) ABSTRACT

A bathing preparation comprising an alkyl phthalide and/or an alkoxy phthalide and/or an alkylidene phthalide optionally together with carbon dioxide gas or a material capable of generating carbon dioxide gas and an extract of a plant belonging to the family Umbelliferae is disclosed. This bathing preparation has excellent effects of warming, retaining the warmth and accelerating blood circulation.

1 Claim, 1 Drawing Sheet

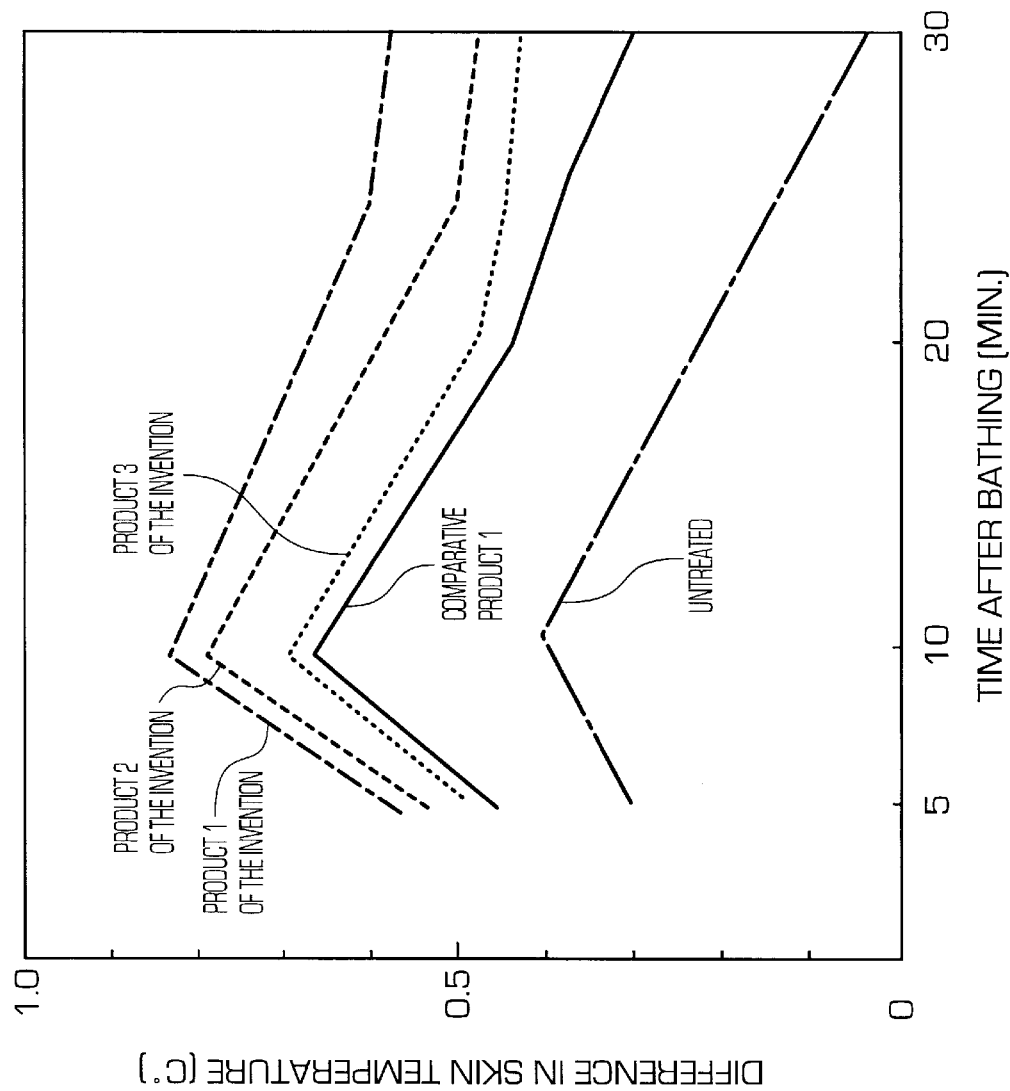

BATHING PREPARATION

This is a Continuation of application Ser. No. 07/794,851 filed Nov. 21, 1991, now abandoned, which is a Continuation of application Ser. No. 07/401,695 filed Sep. 1, 1989, now abandoned.

FIELD OF THE INVENTION

This invention relates to a novel bathing preparation which exhibits excellent effects of warming and retaining the warmth.

BACKGROUND OF THE INVENTION

There have been produced a number of bathing preparations containing various materials such as inorganic salts, crude drugs, oils, enzymes, perfumes and colorants. It has been known for a long time that crude drugs, in particular, herbs, would exert excellent bathing effects, for example, a warming effect when added to a bath. Thus, bathing preparations comprising fine herb pieces packaged in bags or those containing herb extracts are marketed today.

Among these herbs, furthermore, it has been known that rhizomes or roots of plants belonging to the family Umbelliferae such as *Cnidium rhizoma* or *Augelicae radix*, which have been widely employed as crude drugs for a long time, would have excellent bathing effects.

In order to achieve satisfactory bathing effects by using a crude drug of a plant belonging to the family Umbelliferae such as *Cnidium rhizoma* or *Angelicae radix*, however, it is required to use a large amount of the same, which brings about some problems. Namely, the addition of such a large amount of the herb might make the bath turbid. In addition, the large unit usage makes the application thereof inconvenient.

Thus it has been proposed to use an extract obtained by extracting a crude drug with, for example, hot water or a water/alcohol mixture as described, for example, in JP-A-63-246319 (the term "JP-A" as used herein means an "unexamined published Japanese Patent Application"). However the problem of the turbidity of the bath cannot be solved thereby. On the contrary, this process is accompanied by some problems such as the extraction procedure deteriorates the bathing effects and it is disadvantageous from an economical viewpoint.

In addition, the characteristic odor of a bathing preparation containing these herbs makes it such that it is not always favorable for everybody, which is an additional problem from the viewpoint of commercial preference.

SUMMARY OF THE INVENTION

Under these circumstances, we have conducted extensive studies in order to develop an inexpensive bathing preparation which has bathing effects comparable to or even exceeding those of crude drugs and is free from any one of the above-mentioned problems. As a result, we have found that an alkyl phthalide or an alkoxy phthalide represented by the following formula (I) or an alkylidene phthalide represented by the following formula (II) has excellent effects of accelerating blood circulation, warming and retaining the warmth, thus completing the present invention.

Accordingly, the present invention provides a bathing preparation which comprises an alkyl phthalide and/or an alkoxy phthalide represented by the following formula (I):

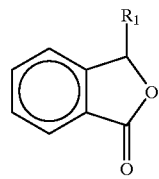

wherein
  $R_1$ represents an alkyl or an alkoxy group having 3 to 14 carbon atoms;
  and/or an alkylidene phthalide represented by the following formula (II):

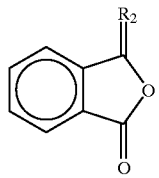

wherein
  $R_2$ represents an alkylidene group having 3 to 14 carbon atoms.

BRIEF DESCRIPTION OF THE DRAWINGS

FIG. 1 shows changes in the temperature of the surface of the skin of panelists after taking various baths.

DETAILED DESCRIPTION OF THE INVENTION

In the present invention, either an alkyl phthalide, an alkoxy phthalide or an alkylidene phthalide represented by the above formulae (I) or (II) may be used. From the viewpoint of stability and sustained activity, however, an alkyl phthalide is preferred. Further, an alkyl phthalide wherein $R_2$ having 4 to 7 carbon atoms is preferable when taking the production process into consideration.

Specific, but non-limiting examples of the alkyl phthalide, alkoxy phthalide and alkylidene phthalide of the present invention include propyl phthalide, butyl phthalide, isoamyl phthalide, heptyl phthalide, octyl phthalide, dodecyl phthalide and tetradecyl phthalide as the alkyl phthalide; propoxy phthalide and isopropoxy phthalide as the alkoxy phthalide; and butylidene phthalide and dodecylidene phthalide as the alkylidene phthalide.

Some of the alkyl phthalides, alkoxy phthalides, and alkylidene phthalides may be extracted from the rhizomes or roots of plants belonging to the family Umbelliferae. Alternately, they may be synthesized by known methods, for example, by reacting phthalic anhydride with a dialkyl cadmium.

As the solvent for extraction of the alkyl phthalide, the alkoxy phthalide or the alkylidene phthalide from the rhizomes or roots of plants belonging to the family Umbelliferae, an organic solvent is suitably used in viewpoint of yield of the compounds. Examples of the organic solvent for the extraction include lower alcohols having 1 to 6 carbon atoms (e.g., methanol, ethanol, n-propanol, isopropanol, n-butanol, sec-butanol and tert-butanol), acetone, acetonitrile, petroleum ether, n-hexane, benzene, toluene, ethers, chloroform and dichloromethane. Among them, a polar organic solvent is preferred.

The methods for synthesis of the alkyl phthalide, alkoxy phthalide or alkylidene phthalide are further disclosed, for example, in *Synthesis, Properties and Molecular Structure of Alkylidene phthalides*, Bull. Inst. Chem., Academia Sinica, Number 31, pages 9 to 15 (March 1984).

Either one of the alkyl, alkoxy and alkylidene phthalides or a mixture thereof may be used in the present invention. These substances are preferably used in such an amount as to give a concentration in a bath of 0.03 to 55 ppm, more preferably 0.3 to 15 ppm. When the concentration thereof is lower than 0.03 ppm, the satisfactory effects of accelerating blood circulation, warming or retaining the warmth cannot be achieved. When it exceeds 55 ppm, on the other hand, the preference of the product might be lowered because the characteristic odor thereof is strengthened.

The use of an extract of a plant belonging to the family Umbelliferae together with the alkyl phthalide, alkoxy phthalide and alkylidene phthalide elevates the effects of warming and retaining the warmth. Furthermore, additional effects characteristic to the extract can be obtained in this case. Examples of plants belonging to the family Umbelliferae suitable for use in the present invention include *Cnidium officinale* MAKINO, *Ligsticum officinale* KITAMURA, *Conioselinum officinale, Ligsticum wallichii* FRANCH, *Ligsticum chauxiong* HORT, *Angelica grosseserrrata* MAXIH, *Angelica polimarpha* MAXIH, *Conioselium univittatum* TURCZ, *Ligsticum sinensis* OLIV, *Ligsticum actilobum* SEBOLD et ZUCCARINI, *Angelica actiloba* KITAGAWA, *Angelica actiloba* KITAGAWA var *sugiymae* HIKINO, *Angelica actiloba* forma *tsukubana, Angelica actiloba* var *iwatensis, Angelica polymorpha* MAXIMOWICZ var *sinesis* OLIVER, *Angelica sinensis* DIELS, *Angelica Uchiyama* YABE, *Angelica taxiioliala* DIELS, *Angelica anomala* LALLEM, *Angelica tschiliensis* WOLFF, *Angelica valida* DIELS, *Heracleum candicans* WALL, *Angelica uchiyama* YABE and *Angelica archangelica* LINN.

The addition of an extract of a plant belonging to the family Umbelliferae to a bath at a high concentration causes turbidity and an intense odor of the crude drug, as described above. Therefore it is preferable to add the extract at such a level as to give a concentration in the bath of 30 ppm or below.

The above-mentioned effect of the bathing preparation can be further improved by introducing carbon dioxide gas into, or by using a material capable of generating carbon dioxide gas together with the bathing preparation comprising the alkyl phthalide, alkoxy phthalide and/or alkylidene phthalide and the extract of the plant belonging to the family Umbelliferae. Furthermore, these effects may be improved by controlling the pH value of a bath containing the bathing preparation at a weakly acidic pH value.

Carbon dioxide gas may be introduced into the bathing preparation of the present invention by charging a sealed container with the bathing preparation and blowing the carbon dioxide gas into the container under one atmospheric pressure or above.

As the material capable of generating carbon dioxide gas, a combination of a carbonate and an acid is preferable. Examples of the carbonate include sodium hydrogencarbonate, sodium carbonate, sodium sesquicarbonate, potassium hydrogencarbonate, potassium carbonate, potassium sesquicarbonate, ammonium hydrogencarbonate, ammonium carbonate and ammonium sesquicarbonate. Either one of these compounds or a mixture thereof may be used.

AS the above-mentioned acid, either an organic or an inorganic acid may be used. It is preferable to use a solid acid soluble in water. Particularly suitable examples thereof include aliphatic dicarboxylic acids such as succinic acid and adipic acid; fumaric acid; phosphoric acid and acidic salts thereof.

The carbonate and acid may be used respectively in amounts of 5 to 80% by weight, in particular 10 to 50% by weight, and 10 to 80% by weight, in particular 15 to 50% by weight, each based on the total composition of the bathing preparation.

It is preferable that a 0.01% by weight aqueous solution of the bathing preparation of the present invention is weakly acidic. More particularly, it is preferable that the aqueous solution has a pH value ranging from 4 to 7, more preferably from 6.0 to 6.7.

The bathing preparation of the present invention may be appropriately formulated into, for example, powders, granules, crystals or tablets. In addition, it may further contain various components commonly used in bathing preparations, for example, inorganic salts such as sodium chloride, potassium chloride, ammonium chloride, sodium sulfate, aluminum sulfate, iron sulfate, sodium carbonate, sodium hydrogencarbonate, calcium carbonate, magnesium carbonate, sodium sesquicarbonate, sulfur, sodium sulfide, potassium sulfide, sodium phosphate, sodium polyphosphate and sodium thiosulfate, enzymes, emollients, humectants, perfumes and colorants.

Accordingly, the present invention makes it possible to obtain an inexpensive bathing preparation which exerts excellent effects of accelerating blood circulation, warming and retaining the warmth, can be conveniently used, causes no turbidity of the bath and has a preferable odor and color.

Although the mechanism of the achievement of these effects by the alkyl, alkoxy and alkylidene phthalides has not been clarified in detail so far, it is believed that these compounds might directly affect the skin so as to accelerate blood circulation and exert some effect on the central nervous system when breathed into the body.

The present invention is now illustrated in greater detail by way of the following Examples, but it should be understood that the present invention is not deemed to be limited thereto.

EXAMPLE 1

Eight healthy male panelists took a bath (180 l) at 40° C. for 10 minutes. The temperature of the surface of the skin of each panelist was determined by thermography prior to the bathing and 10 and 30 minutes thereafter. Thus, the change in the skin temperature caused by the bathing was measured and Table 1 shows the results.

TABLE 1

| Bath | Concentration (g/180 l) | $\Delta T$ (° C.) after 10 min. | $\Delta T$ (° C.) after 30 min. |
|---|---|---|---|
| Untreated | — | 0.38 | 0.02 |
| Cut *Cnidium rhizoma*\* | 30.0 | 0.63 | 0.31 |
| Butyl phthalide | 0.18 | 0.71 | 0.43 |
| Butyl phthalide | 0.09 | 0.69 | 0.39 |
| Butyl phthalide | 1.80 | 0.75 | 0.47 |
| Heptyl phthalide | 0.18 | 0.83 | 0.57 |
| Butylidene phthalide | 0.18 | 0.76 | 0.49 |

TABLE 1-continued

| Bath | Concentration (g/180 l) | ΔT (° C.) after 10 min. | ΔT (° C.) after 30 min. |
|---|---|---|---|
| Pentylidene phthalide | 0.18 | 0.78 | 0.53 |
| Isoamyl phthalide | 0.18 | 0.73 | 0.45 |
| Propoxy phthalide | 0.18 | 0.82 | 0.50 |

*"*Cnidium rhizoma*" as used herein is defined in Japanese Pharmacopeia

EXAMPLE 2

The warming effects and amounts of precipitates of various baths were determined by the following methods.

Warming Effect

A panelist took a bath (180 l) at 40° C. for 10 minutes. When the temperature of the surface of the skin of the panelist 10 minutes after the bathing was higher than that before the bathing by 4.5° C. or more, the warming effect was referred to as positive (o).

Precipitate

Each sample was homogeneously dissolved and transferred to a graduated centrifuging tube. The total volume of the solution was adjusted to 50 ml. Next, it was centrifuged at 20° C. at 3000 rpm for 10 minutes and the precipitate thus formed was determined.

The results are shown in Table 2.

TABLE 2

| Butyl phthalide (g/180 l) | Cnidium rhizoma extract (g/180 l) | Warming effect | Precipitate (cc) | Odor |
|---|---|---|---|---|
| 0 | 10 | o | 9.4 | Excessively intense odor of crude drug. |
| 0.1 | 7.5 | o | 7.2 | Intense odor of crude drug. |
| 0.2 | 5 | o | 4.7 | Some odor of crude drug, not unpleasant. |
| 0.3 | 2.5 | o | 2.2 | Some odor of crude drug. |
| 0.4 | 0 | o | 0 | Odor of phthalide. |

EXAMPLE 3

(Bathing Preparation)

Product 1 of the Invention 0.81 g of butyl phthalide was mixed with 0.005 of sucrose stearate and dextrin was added thereto to obtain 2.5 g of a powdery bathing preparation.

Product 2 of the Invention

To the above product 1 of the invention were added 32.0 g of sodium hydrogencarbonate and 15.5 g of succinic acid. The mixture obtained was molded into tablets each weighing 50 g.

Product 3 of the Invention

To the above product 1 of the invention were added 29.0 g of sodium hydrogencarbonate, 13.5 g of succinic acid and 5 g of a dry powder of *Cnidium rhizoma* extract, which had been prepared by extracting *Cnidium rhizoma* as defined in Japanese Pharmacopeia with hot water in a conventional manner and spray drying the obtained extract. The mixture thus obtained was formulated into tablets each weighing 50 g.

Comparative Product 1

Official *Cnidium rhizoma* was cut with a grinder to thereby give a diameter of approximately 5 mmφ. 30 g portions of the cut *Cnidium rhizoma* were packed into bags to thereby give a bathing preparation.

Evaluation of Effects of Warming and Retaining the Warmth

Eight healthy male panelists took a bath (180 l) at 40° C. containing product 1, 2 or 3 of the invention or the comparative product 1 for 10 minutes. After bathing, the change in the temperature of the surface of the skin of each panelist was monitored by thermography over time. Products 1 to 3 of the invention were used each in such an amount as to give a concentration of butyl phthalide in the bath of 1 ppm, while 30 g of the comparative product 1 was added to 180 l of the bath. FIG. 1 shows the results.

EXAMPLE 4

The hair from the breast to the abdomen of an etherized rabbit was removed and the trachea of the animal was opened. The animal was subjected to artificial respiration. Next, the rabbit was provided with an adaptor for the determination of skin blood flow and 0.02 g of sample A and sample B described below was added dropwise to the adaptor. The change in the amount of blood flow was monitored by the Laser Doppler method. Table 3 shows the results where each value represents the relative amount of blood flow 20 minutes after initiation of the treatment. The amount of the blood stream immediately before initiation of the treatment was taken as 100%. As Table 3 indicates, both the butyl phthalide and heptyl phthalide are effective in accelerating blood circulation.

Sample A: butyl phthalide (stock solution).

Sample B: heptyl phthalide (stock solution).

TABLE 3

| Sample | Mean ± Standard Error (%) |
|---|---|
| A | 148.4 ± 18.0 |
| B | 200.8 ± 44.3 |

(Number of Experiments: 5)

While the invention has been described in detail and with reference to specific examples thereof, it will be apparent to one skilled in the art that various changes and modifications can be made therein without departing from the spirit and scope thereof.

What is claimed is:

1. A method for accelerating blood circulation, warming the human body and improving the retention of the warmth which comprises bathing the body in a bath containing a bathing preparation comprising at least one compound selected from the group consisting of an alkyl phthalide, an alkoxy phthalide, an alkylidene phthalide and a mixture thereof, wherein the alkyl phthalide and the alkoxy phthalide are represented by the following formula (I):

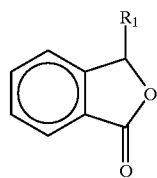 (I)

wherein

R$_1$ represents an alkyl or an alkoxy group having 3 to 14 carbon atoms;

and the alkylidene phthalide is represented by the following formula (II):

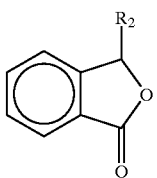 (II)

wherein
R$_2$ represents an alkylidene group having 3 to 14 carbon atoms,
wherein
said alkyl phthalide, alkoxy phthalide, alkylidene phthalide or mixture thereof is present in an amount effective to achieve the functions of accelerating blood circulation, warming the human body and improving retention of the warmth which is an amount which gives a concentration thereof in a bath of 0.03 to 55 ppm.

* * * * *